United States Patent
Johns et al.

(10) Patent No.: US 9,669,146 B2
(45) Date of Patent: Jun. 6, 2017

(54) GAS / FLUID MASS EXCHANGE APPARATUS

(75) Inventors: William Richard Johns, Berkshire (GB); Stephen Warwick James Brown, Powys (GB); Richard Phillips, Glamorgan (GB); Dale Rogers, West Glamorgan (GB)

(73) Assignee: HAEMAIR LIMITED, South Wales (GB)

(*) Notice: Subject to any disclaimer, the term of this patent is extended or adjusted under 35 U.S.C. 154(b) by 538 days.

(21) Appl. No.: 14/118,996

(22) PCT Filed: May 15, 2012

(86) PCT No.: PCT/GB2012/051077
§ 371 (c)(1),
(2), (4) Date: Mar. 5, 2014

(87) PCT Pub. No.: WO2012/160347
PCT Pub. Date: Nov. 29, 2012

(65) Prior Publication Data
US 2014/0353854 A1    Dec. 4, 2014

(30) Foreign Application Priority Data
May 20, 2011 (GB) .................................. 1108495.1

(51) Int. Cl.
B01F 3/04    (2006.01)
A61M 1/16   (2006.01)
B01D 63/08  (2006.01)

(52) U.S. Cl.
CPC ........... *A61M 1/1698* (2013.01); *B01D 63/08* (2013.01); *B01D 63/082* (2013.01);
(Continued)

(58) Field of Classification Search
CPC ... A61M 1/1698; B01D 63/08; B01D 63/082; B01D 2313/06; B01D 2325/24; B01F 3/04829
(Continued)

(56) References Cited

U.S. PATENT DOCUMENTS 3,522,885 A    8/1970  Lavender et al.
3,651,616 A    3/1972  Blanchard
(Continued)

FOREIGN PATENT DOCUMENTS

CA    1238831    7/1988
EP    0003495    8/1979
(Continued)

OTHER PUBLICATIONS

ISR international Search Report and Written Opinion for PCT/GB2012/051077 filed May 15, 2012.
(Continued)

*Primary Examiner* — Charles Bushey
(74) *Attorney, Agent, or Firm* — Fleit Gibbons Gutman Bongini & Bianco PL; Paul D. Bianco; Gary S. Winer

(57) ABSTRACT

A gas/fluid mass exchange apparatus includes a gas permeable membrane which is arranged to separate a first region for receiving a gas flow, from a second region for receiving a fluid flow. The apparatus further a support element which is arranged to maintain the shape and orientation of the membrane.

24 Claims, 6 Drawing Sheets

(52) U.S. Cl.
CPC ...... *B01F 3/04829* (2013.01); *B01D 2313/06* (2013.01); *B01D 2325/24* (2013.01)

(58) Field of Classification Search
USPC .................................. 261/74, 101, 102, 104
See application file for complete search history.

(56) References Cited

U.S. PATENT DOCUMENTS

| | | | |
|---|---|---|---|
| 3,684,097 A * | 8/1972 | Mathewson, Jr. ... | B01D 63/082 210/321.72 |
| 3,834,544 A | 9/1974 | Tyson | |
| 3,998,593 A * | 12/1976 | Yoshida ............. | A61M 1/1698 128/DIG. 3 |
| 4,239,728 A | 12/1980 | Stenberg | |
| 4,308,230 A * | 12/1981 | Bramson ............. | B01D 63/082 128/DIG. 3 |
| 4,328,102 A | 5/1982 | Bellhouse et al. | |
| 4,411,872 A | 10/1983 | Bramson | |
| 4,663,125 A | 5/1987 | Gordon | |
| 4,666,668 A | 5/1987 | Lidorenko | |
| 4,995,888 A | 2/1991 | Beaupre | |
| 5,270,004 A | 12/1993 | Cosentino | |
| 5,634,892 A | 6/1997 | Whalen | |
| 6,004,511 A | 12/1999 | Biscegli | |
| 6,241,945 B1 * | 6/2001 | Owen ................ | A61M 1/1698 210/252 |
| 8,079,574 B2 * | 12/2011 | Lin .................... | A61M 1/1698 261/104 |
| 2007/0231203 A1 * | 10/2007 | Mizoguchi .......... | A61M 1/1698 422/45 |
| 2009/0081079 A1 | 3/2009 | Johns | |
| 2010/0183865 A1 | 7/2010 | Nagayama | |

FOREIGN PATENT DOCUMENTS

| | | |
|---|---|---|
| EP | 2161127 | 3/2010 |
| EP | 2161127 | 10/2010 |
| FR | 2445163 | 7/1980 |
| GB | 1236648 | 6/1971 |
| GB | 1256936 | 12/1971 |
| GB | 2174912 | 11/1986 |
| WO | 8001043 | 5/1980 |
| WO | 99/59654 | 11/1999 |
| WO | 02/078768 | 10/2002 |
| WO | 2008/107723 | 9/2008 |
| WO | 2012/160347 A2 | 11/2012 |
| WO | 2012/160347 A3 | 11/2012 |

OTHER PUBLICATIONS

Search Report for GB1108495.1 dated Sep. 21, 2011.
Written Opinion. Nov. 2013, for PCT/GB2012/51077.
International Preliminary Report on Patentability, Nov. 2013, for PCT/GB2012/51077.
British Search Report dated Mar. 1, 2013 for GB Application No. GB1208522.1.

* cited by examiner

GAS / FLUID MASS EXCHANGE APPARATUS

FIELD OF THE DISCLOSURE

The present invention relates to a gas/fluid mass exchange apparatus.

BACKGROUND OF THE DISCLOSURE

Gas/fluid mass exchange apparatuses are commonly used in medical practice for transferring oxygen from air to a blood supply and carbon dioxide from blood to the air. Such devices are typically referred to as oxygenators and most frequently employ pure oxygen as the gas phase. However, none of the designs build on the fundamental science that determines the most effective arrangement of components. The basic principles that must be observed are:
1. Minimize the risk of blood clots forming within or being stimulated by the flow through the mass exchanger;
2. Maximize the mass transfer rates of oxygen and carbon dioxide within the exchanger; and,
3. Minimize the volume of blood in the exchanger (that is the volume of blood outside the body).
4. Minimize pressure drop across the exchanger.

The risk of blood clots can be minimized by applying a treatment to the surface of all materials contacting blood. The surface can be either non-thrombogenic or anti-thrombogenic, or can combine non-thrombogenic and anti-thrombogenic properties. However, no surface completely eliminates the risk of clots forming when the blood flows outside the veins. The rheology of blood changes whilst it passes through any medical device and it clots at a rate determined by the characteristics of the blood and of the surfaces with which it is in contact.

In order to maximize mass transfer rates, the blood flow characteristics must be understood. In particular, any design must recognize that the majority of the blood flow will be laminar. The laminar characteristics of the flow are made clear by reference to the relevant Reynolds Number, namely:

$$Re = \rho u d / \mu$$

where
- Re is the Reynolds Number
- $\rho$ is the fluid density
- u is the fluid velocity
- d is a characteristic linear dimension (for example, the diameter of a tube)
- $\mu$ is the fluid viscosity Blood is a non-Newtonian fluid, but for the purpose of estimating Reynolds Number an apparent viscosity can be taken. In this respect, at a temperature of approximately 37° C., the value of the Reynolds Number typically resides in the range 0.06<Re<12.

The turbulent flow transition occurs at a Reynolds Number of around 2,000. Hence, within a large margin, the flow is substantially laminar. The non-Newtonian nature of blood introduces uncertainty, but the margin to laminar flow is so great that it can be assured that flow remains substantially laminar. Under laminar conditions, mass transfer is essentially by diffusion, which is similar to heat transfer by conduction, and for geometrically similar flow patterns, both heat transfer and mass transfer coefficients are found to be inversely proportional to a characteristic linear dimension. For flow through tubes of circular cross-section, Coulson & Richardson ("Chemical Engineering", Volume 1, 6th Edition, p 425, equation (9.80)) derive the relationship for heat transfer as:

$$h = 4.1 k/d$$

where "h" is the heat transfer coefficient, "k" is the thermal conductivity, and "d" is the inner diameter of the tube. The corresponding equation for mass transfer is:

$$U = 4.1 D/d$$

where "U" is the mass transfer coefficient, and "D" is the diffusivity of the material being transferred within the bulk fluid through which it is transferred. Similar equations apply for other geometries, but with different values of the numerical coefficient.

In gas/fluid or more particularly, gas/blood mass exchange, the linear dimensions are very small compared to the length with typical length/diameter ratios of 50 to 200. Hence, the end and exit effects are small, and no correction needs to be made for the effect. In practice, blood is non-Newtonian and the flow patterns may be more complex. However, it still follows that mass transfer coefficients are almost independent of Reynolds Number and hence of fluid velocity. It further follows that mass transfer rates depend primarily on interfacial area, driving force (difference between gas phase pressure and equilibrium partial pressure), and the mean width of the flow channels.

U.S. Pat. No. 6,004,511 discloses a gas/fluid mass exchanger in which a blood supply is passed from a patient, through a flow region comprising a plurality of closely packed gas permeable flow ducts through which air arranged to pass. The oxygenated blood with depleted carbon dioxide is then returned to the patient. The diffusivity of gas to and from blood across the flow ducts is known to depend on the viscosity of the blood, such that for example as blood clots, its apparent viscosity increases and the diffusivities of oxygen and carbon dioxide would be expected to decrease. Clot growth is initiated at the surfaces over which blood flows and so a slow blood flow at a surface presents two major problems. These include the intrinsic risk that clots present to the well-being of a person and that the presence of clots increases the effective viscosity of the blood, so that molecular movement is hindered and the diffusivities are reduced.

The blood clotting process progresses when blood leaves the blood vessels and travels over a foreign surface, such as a mass exchanger surface. The longer the blood is out of the blood vessels, the greater the risk and extent of blood clotting. It follows that the longer the residence time of blood out of the blood vessels, the greater is the risk that harmful clots will be returned to the body, with both detrimental impact on a patient's health and risk that a clot will cause death. As part of the clotting process, the apparent viscosity of the blood increases, and the longer the blood is out of the body, the further this thickening process proceeds. This thickening has a detrimental impact on mass exchanger performance because increasing viscosity decreases the diffusivities of oxygen and carbon dioxide in the blood. Reduced diffusivity results in reduced mass transfer and reduced exchanger performance. There are therefore strong incentives to minimize blood residence time in such a mass exchanger.

U.S. Pat. No. 6,004,511 discloses a gas/fluid mass exchanger comprising a plurality of hollow fibres which are packed closely together in touching relation, to maximize the total surface fibre area per unit volume. The effect of close-packed fibres is illustrated in FIG. 1 of the drawings, which presents a sectional view across a known mass exchanger 10. In this illustration, air is fed through narrow tubes 11 and blood is passed around them. The regions 12 (illustrated as shaded) adjacent to where the fibres touch 13 give rise to slow blood flows. Blood clots 14 can readily develop in regions where the blood flow becomes stagnant or near-stagnant. In order to transfer from the free flowing stream to the membrane surfaces, the dissolved gas must diffuse through these stagnant or clotted areas. The long transfer paths almost tangential to the fibre surface, result in low mass transfers coefficients. Thus, these shaded regions effectively block mass transfer giving rise to reduced effective mass transfer area.

The hollow fibres and membranes typically used in mass exchange apparatuses are necessarily thin to enable the gas molecules to pass therethrough. However, the thin form of the fibres makes for a flexible fibre which can move and touch neighbouring fibres, under the fluid flow and thus trap blood in the interstices, which can lead to the above mentioned problems. This problem is overcome in some commercial applications by supplying fibres wound into a mat comprising supporting fibres which maintain a defined separation between the hollow fibres. These include for example, the Celgard X30-24 and the Oxyplus 90/200 hollow fibres. Such mats have the disadvantage that the supporting fibres making up the mats are nearly normal to the blood flow and produce local areas of virtually zero flow at each connection, thus giving both long residence times and a high surface area with no mass transfer, which present opportunities for blood clot growth.

SUMMARY OF THE DISCLOSURE

According to a first aspect of the present invention there is provided a gas/fluid mass exchange apparatus, the apparatus comprising a gas permeable membrane which is arranged to separate a first region for receiving a gas flow, from a second region for receiving a fluid flow, wherein the apparatus further comprises support means which is arranged to maintain the shape and orientation of the membrane.

Advantageously, the support means is arranged to minimise any flexing of the membrane under the gas and fluid flow, thereby preserving the shape and orientation of the membrane. This ensures that adjacent membranes do not touch, since this would otherwise obscure the mass transfer area and cause a reduced flow rate which is known to increase the risk of clotting. In addition, the exchange apparatus provides for a reduced residence time for blood flow therethrough, thereby further reducing the potential for clot development.

Current blood/gas mass exchangers all have unequal path lengths and wide residence time distributions because some volumes within the exchanger have blood with very low velocities, or which is almost stagnant. The current invention eliminates such unequal path lengths and minimizes features that give volumes with slow blood velocity. The exchange apparatus of the present invention further provides for an increased mass transfer surface area per unit volume, since the blood held between two flat surfaces experiences a higher area per unit volume than known transfer fibres.

Preferably, the support means comprises a support member disposed upon the membrane. The support member is preferably arranged to extend along the membrane and is preferably bonded upon the membrane.

The membrane preferably comprises a plurality of support members disposed thereon.

Preferably, the or each support member comprises a wire.

Preferably, the or each support member is disposed on the side of the membrane which is arranged to face the first region. The fluid flow, such as a blood flow, is thus exposed to a smooth membrane surface to provide for a substantially laminar flow in the second region, and thus minimise possible nucleation sites for blood clots, for example, to develop. In this case, a smooth membrane is defined as one in which the surface does not comprise micro-pores or a membrane in which the micro-pores do not extend to the surface.

Alternatively or in addition thereto, the support means preferably comprises or further comprises means for tensioning the membrane.

Preferably, the membrane comprises a substantially planar membrane.

Preferably, the first and second regions are substantially sealed from each other, such that the fluid in the second region is prevented from passing into the first region.

The gas flow within the first region and the fluid flow within the second region comprise substantially parallel flow directions. In this respect, the gas and blood flow, for example may be in the same direction or in substantially opposite directions.

Preferably, the membrane is further supported at a periphery thereof by a frame, which preferably extends around the periphery of the membrane. The membrane is preferably sealed to the frame.

The frame is preferably arranged to support a first membrane at a first side thereof and a second membrane at a second side thereof to define a gas/fluid exchange unit. The support members disposed on the membranes further enable the membranes to be positioned close together, but spaced from each other, to maximise the surface area for mass exchange.

The apparatus preferably comprise a plurality of gas/fluid exchange units which are preferably spaced apart by a plurality of spacer elements. The spacer elements preferably extend along opposite sides of the units to define a flow path between the first membrane of one unit and a second membrane of the adjacent unit.

In an alternative embodiment, the support member preferably comprises a substantially planar porous sheet comprising an increased porosity compared with the membrane. Preferably, the sheet comprises a loosely woven material.

The sheet is preferably arranged to support a first membrane at a first side thereof and a second membrane at a second side thereof.

Preferably, the first and second membranes of the alternative embodiment are sealed along a respective periphery thereof to the sheet to define an alternative gas/fluid exchange unit.

The exchange apparatus of the alternative embodiment, preferably comprises a plurality of alternative gas/fluid exchange units which are preferably spaced apart by a plurality of spacer elements.

Preferably, the spacer elements are arranged to extend along opposite sides of the alternative units to define a flow path between the first membrane of one alternative unit and a second membrane of the adjacent alternative unit.

The apparatus preferably further comprises a gas inlet housing for passing gas into the or each first region and a gas outlet housing for passing gas out from the or each first region.

The apparatus preferably further comprises a fluid inlet housing for passing fluid into the or each second region and a fluid outlet housing for passing fluid out from the or each second region.

The gas preferably comprises a mixture of oxygen and carbon dioxide, and the fluid preferably comprises a liquid, such as blood, such that upon passing blood through the or each second region, oxygen in the or each first region disposed adjacent the respective second region, can pass across the membrane therebetween to oxygenate the blood, and carbon dioxide within the blood can pass in the opposite direction across the membrane into the respective first region.

The gas may further comprise an inert gas, such as nitrogen, in addition to the oxygen and carbon dioxide. For use as a respiratory aid, oxygen is arranged to pass through the membrane from the gas phase into the blood flow and carbon dioxide is arranged to pass, in the opposite direction through the membrane from the blood flow into the gas phase. In this application, the inert gas is arranged to provide a means of controlling the rate of oxygen transfer and the carbon dioxide in the gas phase is present to limit the amount of carbon dioxide stripped from the blood.

It is envisaged that the exchange apparatus may find other applications in which blood properties depend on the blood gas concentrations, and when it is desired to control such blood gas concentrations to measure the properties under controlled conditions. In such applications, alternative gas mixtures may be required to provide the control of blood gas concentrations to required levels. It is also envisaged that the exchange apparatus may find other applications with other non-Newtonian liquids, such as foodstuffs and biochemical solutions or suspensions, where excessively long residence times may adversely affect the product.

According to a second embodiment of the present invention there is provided a gas/fluid mass exchange apparatus, the apparatus comprising a housing and plurality of gas permeable flow ducts which are arranged to extend through a fluid flow region of the housing between a gas inlet and a gas outlet of the housing, the apparatus further comprising a fluid inlet for receiving fluid into the fluid flow region of the housing and a fluid outlet for passing fluid out from the fluid flow region, the flow ducts being held in spaced relation with respect to each other, wherein, the fluid inlet and fluid outlet are separated from the fluid flow region by a fluid inlet and a fluid outlet manifold, which are contoured to conform with contours of the fluid inlet and fluid outlet respectively, at an interface therebetween.

Advantageously, the exchange apparatus of the second aspect, provides for gas flow ducts which are spaced apart from each other so that the fluid, for example blood, can pass easily around the flow ducts, without becoming stagnant. Moreover, the uncoupled nature of the flow ducts within the flow region, further minimises the development of clots for example, when blood is passed through the flow region.

The ideal flow pattern through the apparatus would be for every element of blood entering the exchange apparatus to follow an exactly equal path length, with equal velocity and with exactly equal residence time between entry and exit. Any feature that increases the residence time of an element of blood, relative to other elements, gives that element a higher risk of clotting within the exchange apparatus. Since elements of liquid which flow nearer to surfaces travel more slowly than elements further from surfaces, minimizing surface features facilitates a reduction in clot development. The apparatus of the second embodiment provides for an improved fluid flow therethrough by providing a contoured fluid inlet and outlet manifold which serves to direct the fluid from the fluid inlet to the fluid outlet.

The flow ducts are preferably uncoupled from each other within the fluid flow region.

Preferably, the flow ducts comprise substantially tubular flow ducts, formed of a gas permeable membrane.

The flow ducts preferably comprise at least one support member disposed thereon. Preferably, the at least one support member extends along the flow duct. The support member is preferably arranged to maintain the shape and orientation of the flow duct.

Preferably, the fluid inlet manifold is contoured to direct the fluid into the fluid flow region in a direction which is substantially along the flow ducts. This arrangement, as described in the introductory paragraphs, minimises stagnant fluid and any recycling of the fluid flow, and hence minimises the risk of blood clots developing whilst also ensuring that mass transfer coefficients are not reduced by having near-zero flow in parts of the exchanger.

In an alternative embodiment, the fluid inlet manifold is preferably contoured to direct the fluid into the fluid flow region in a direction which is substantially across the flow ducts.

Preferably, the fluid inlet manifold of the alternative embodiment comprises a fluid flow channel having a proximal end disposed adjacent the fluid inlet and the fluid flow channel preferably comprises a cross-sectional area which reduces along the length of the channel from the proximal end to a distal end thereof.

Similarly, the fluid outlet manifold of the alternative embodiment preferably comprises a fluid flow channel having a proximal end disposed adjacent the fluid outlet and the channel preferably comprises a cross-sectional area which reduces along the length of the channel from the proximal end to a distal end thereof.

Further preferred features of the gas/fluid mass exchange apparatus of the second embodiment may comprise one or more of the preferred features of the gas/fluid mass exchange apparatus of the first embodiment.

BRIEF DESCRIPTION OF THE DRAWINGS

Embodiments of the present invention will now be described by way of example only and with reference to the accompanying drawings, in which:

FIG. 2a is a perspective view of a gas/fluid mass exchange unit of a gas fluid mass exchange apparatus according to an embodiment of the present invention;

FIG. 2b is a side view of the gas/fluid mass exchange unit illustrated in FIG. 2a;

FIG. 2c is a perspective view of a plurality of gas/fluid mass exchange units of a gas/fluid mass exchange apparatus according to an embodiment of the present invention; and, FIG. 2d is a front view of the gas/fluid mass exchange apparatus illustrated in FIG. 2c;

DETAILED DESCRIPTION OF THE DISCLOSURE

Figure 1:
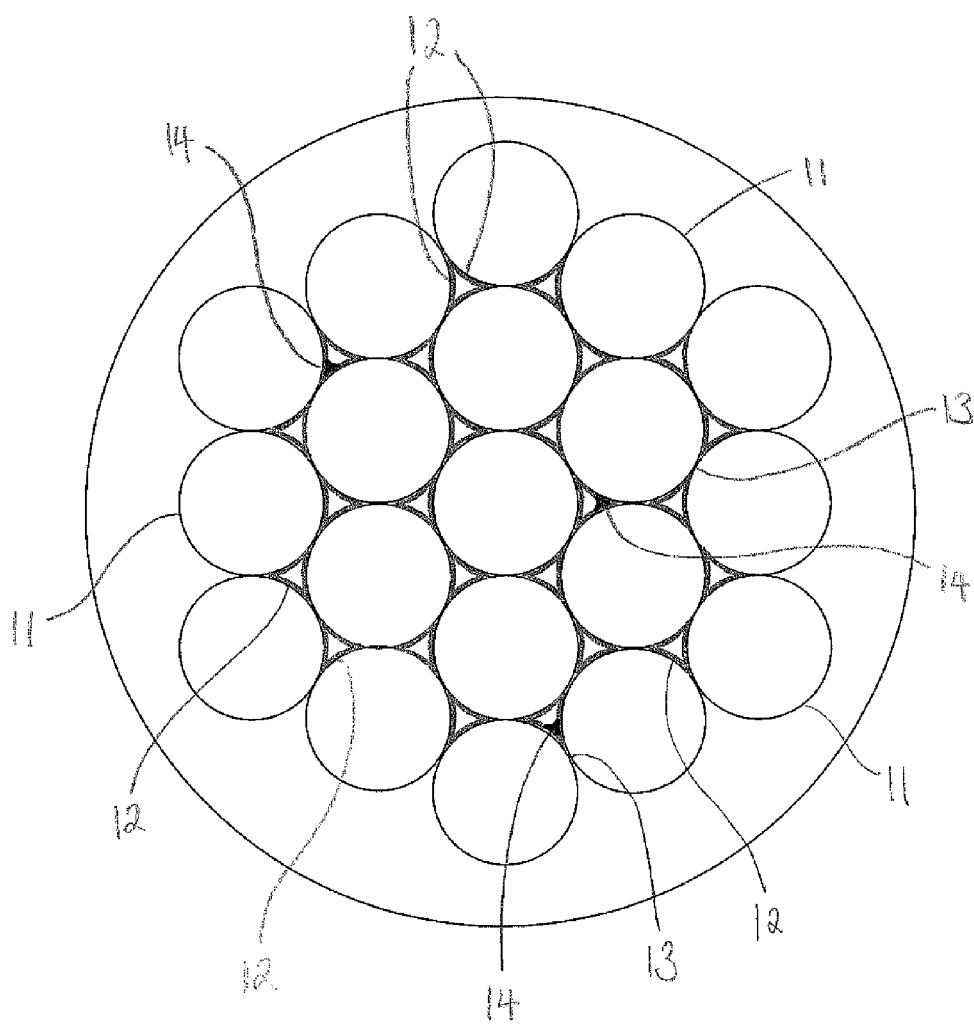
FIG. 1 is a cross-sectional view of a known gas/fluid mass exchange apparatus.
Figure 2:
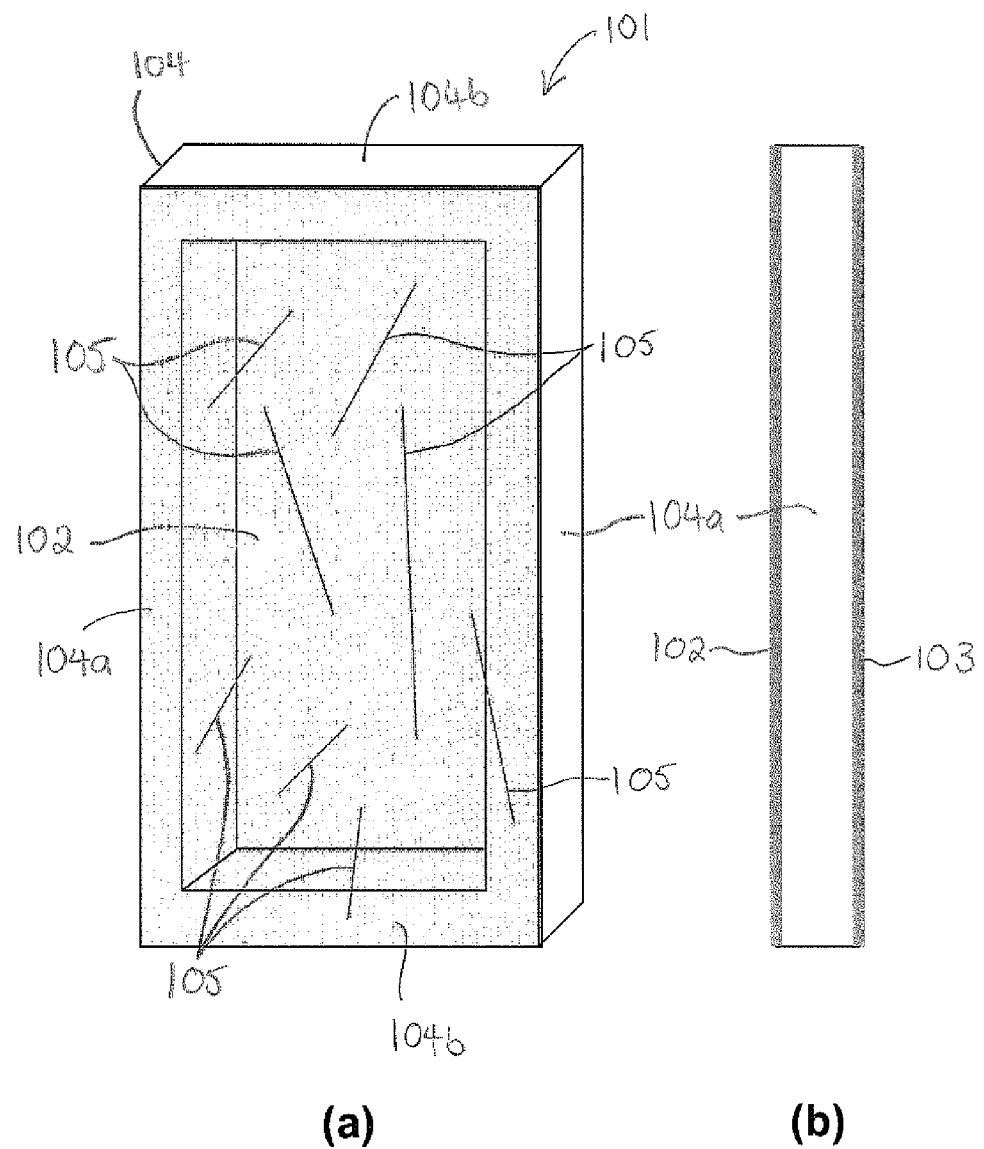
Figure 2:
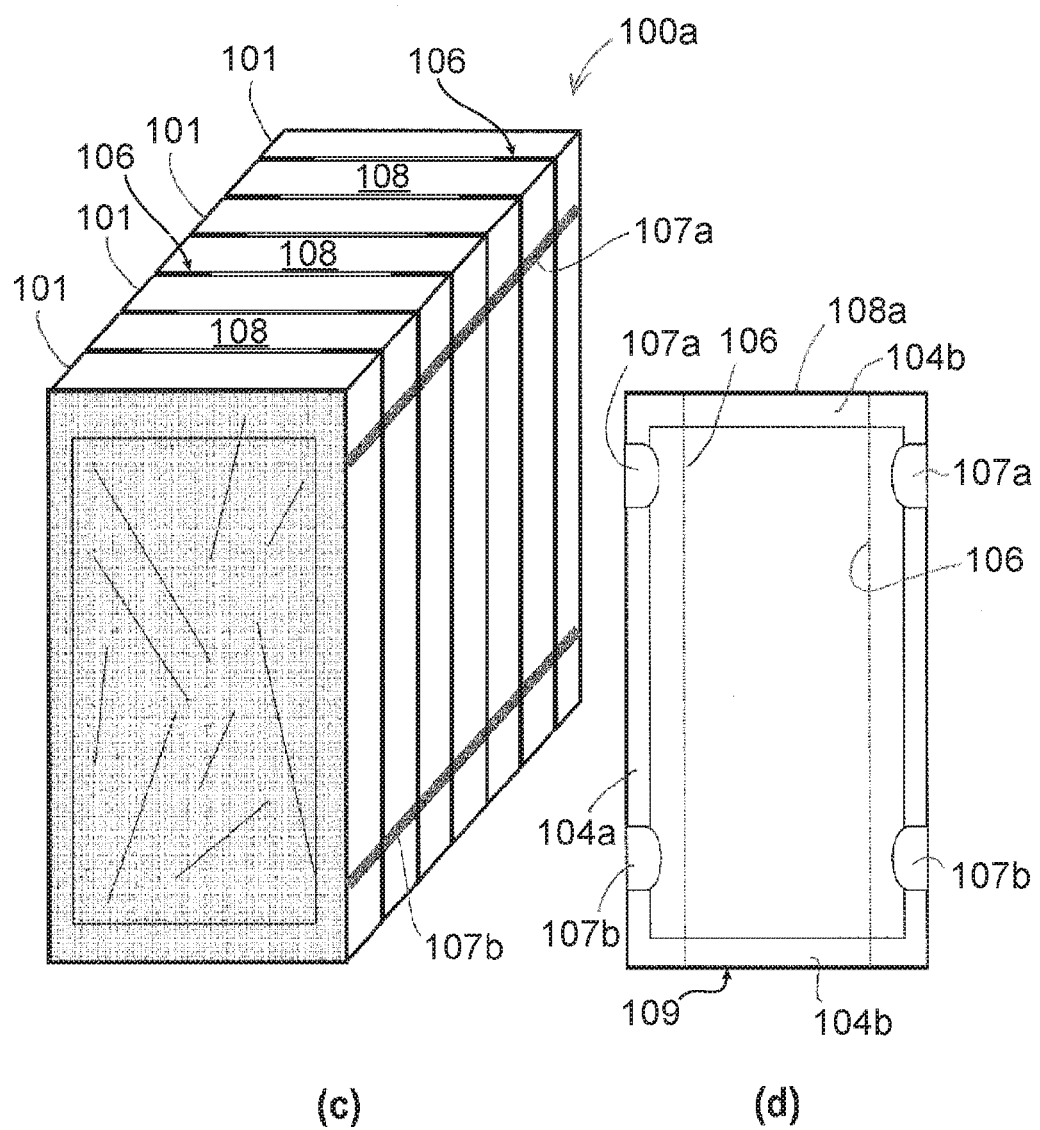

Referring to FIG. 2 of the drawings, there is illustrated a gas/fluid mass exchange apparatus 100a according to a first embodiment of the present invention for enabling the exchange of oxygen and carbon dioxide with a blood flow, for example. In this respect, the apparatus 100 may be used as an oxygenator to oxygenate deoxygenated blood.

The apparatus comprises a plurality of gas/fluid mass exchange units 101, which separately comprise a first and second substantially planar gas permeable membrane 102, 103. The first and second membranes 102, 103 are substantially rectangular in shape and sealed at their periphery to a substantially rectangular frame 104, comprising opposite longitudinal 104a and lateral frame members 104b. The skilled reader will recognise however, that other shapes of membranes and frame may also be used. The first membrane 102 is secured to a first side of the frame 104 and the second membrane 103 is secured to a second side of the frame 104, such that the first and second membranes 102, 103 and frame 104 define a fluid sealed interior space therebetween, as illustrated in FIGS. 2a and 2b of the drawings.

The first and second membranes 102, 103 are arranged to extend in substantially parallel planes, and are separated from each other by the thickness of the frame members 104a, 104b, which may be approximately 100-400 μm, for example. The shape and orientation and thus the separation of the membranes 102, 103 is maintained by a plurality of support members 105, such as sections of wire, which are glued or otherwise bonded to the membranes 102, 103 to increase the rigidity of the respective membrane. The support members 105 are arranged to extend in the plane of the respective membrane 102, 103 and are disposed upon the side of the first and second membrane 102, 103 which faces the interior space of the respective unit 101. In an alternative embodiment which is not illustrated, the shape and orientation of the membranes 102, 103 is maintained by a tensioning assembly (not shown) which is arranged to hold the membranes under tension.

Referring to FIGS. 2c and 2d of the drawings, the exchange units 101 of the first embodiment are coupled together to form a stacked configuration, such that the first and second membranes 102, 103 of the exchange units 101 extend in substantially parallel planes. The units 101 are coupled together by a resin strip 106 which extends between lateral frame members 104b of each unit 101. The resin strips 106 comprise spacer members (not shown) which serve to hold the units 101 in spaced relation, and the strips extend from a position along the longitudinal side member 104a of the frame 104, laterally across the frame 104 to a position disposed upon the first and second membranes 102, 103. In this respect, each resin strip 106 comprises a width which is greater than the width of the longitudinal frame members 104a.

The stacked configuration of units 101 further comprises elongate grooves 107 which extend across the units 101 at an upper and lower region of the longitudinal frame members 104a of the frames 104 of the respective units 101. The grooves 107 extend into the respective units to a depth which is greater than the width of the longitudinal frame members 104a, but which is less than the width of the resin strip 106. The grooves 107 thus establish an inlet 107a and an outlet 107b to the interior space between the first and second membrane 102, 103 of each unit 101.

The resin strip 106 which extends along opposite longitudinal frame members 104a between adjacent units 101 together with the first and second membranes 102, 103 of adjacent units 101, define a fluid flow channel between the units 101, which extends from an inlet 108 defined between upper lateral frame members 104b of adjacent units 101, and an outlet 109 defined between lower lateral frame members 104b of adjacent units 101. The apparatus 100a further comprises a fluid inlet manifold (not shown) which is arranged to extend over the stacked configuration of units 101 to enable a fluid to pass into the flow channels between the units 101 and an outlet manifold (not shown) for collecting the fluid which passes out from the channels. Similarly, the apparatus 100a further comprises a gas inlet manifold (not shown) which is arranged to extend over the grooves 107a disposed at an upper region of the stacked configuration of units 101 to pass gas into the respective units 101 between the respective first and second membrane 102, 103, and a gas outlet manifold (not shown) for collecting the gas which passes out from the groove 107b disposed at the lower region of the stacked configuration of units 101. In this respect, it is evident that the flow of gas extends in a direction which is substantially parallel to the membranes and also, substantially parallel to a blood flow direction.

Figure 2E:
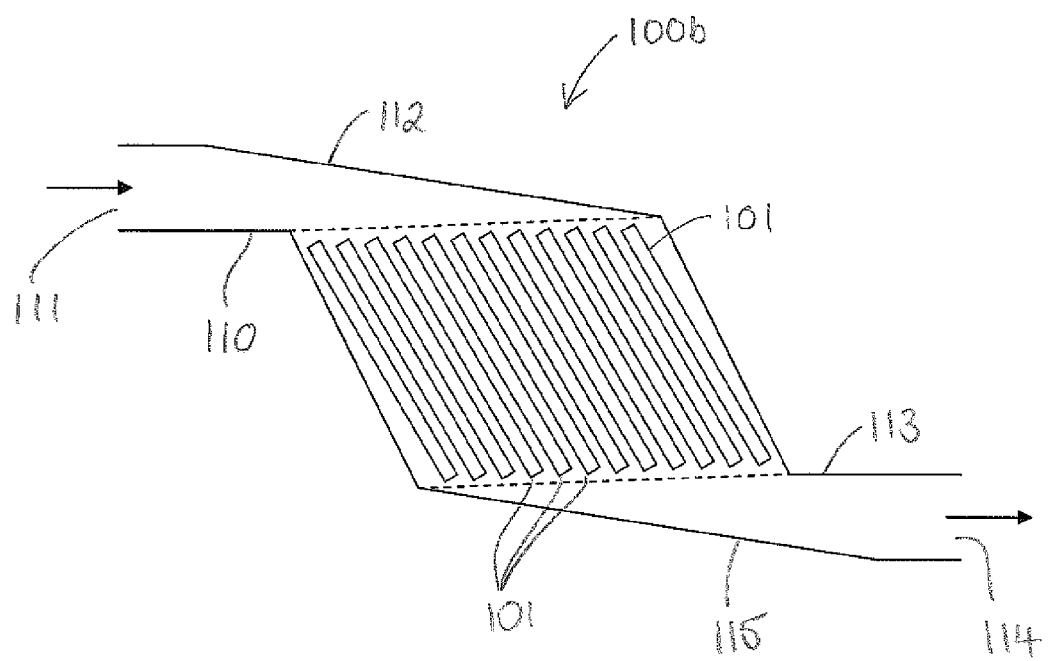
FIG. 2e is a cross-sectional view of a gas/fluid mass exchange apparatus according to an alternative embodiment of the present invention.

Referring to FIG. 2e of the drawings, there is illustrated a gas/fluid mass exchange apparatus 100b according to a second embodiment of the present invention. The apparatus 100b of the second embodiment is substantially the same as the apparatus 100a of the first embodiment and so like features have been referenced using the same numerals.

The units 101 of the exchange apparatus 100b of the second embodiment comprise longitudinal frame members 104a having a reduced length compared with the longitudinal frame members 104a of the units 101 of the first embodiment. The shorter frame members 104a provides a reduced transit path for fluid in passing through the apparatus 100b, compared with the apparatus 100a of the first embodiment, and thus serves to minimise the fluid pressure drop across the apparatus 100b.

The second embodiment of the exchange apparatus 100b comprises an inlet manifold 110 which is arranged to pass fluid between units 101 from an upper region thereof. The inlet manifold 110 comprises an inlet 111 and a housing 112 which is arranged to extend over the upper surface of the apparatus 100. In the embodiment illustrated, the inlet 111 is disposed at the front of the apparatus 100 and the housing 112 is arranged to slope from the inlet 111 toward the units 101, such that as the fluid enters the manifold 110 and passes along the manifold 110, the fluid becomes directed toward the units 101 and thus between the units 101. The housing 112 of the inlet manifold 110 is further arranged to narrow in cross-section along the length thereof such that as the fluid passes along the manifold 110, the velocity of the fluid is substantially maintained to minimise the development of any stagnant volumes within the apparatus 100.

The apparatus of the second embodiment further comprises an outlet manifold 113 having an outlet 114 and a housing 115 which is arranged to extend over the lower region of the apparatus 100. The outlet 114 is disposed at the rear of the apparatus 100, namely diametrically opposite the inlet 111, and the housing 115 is arranged to slope away from the units 101 toward the outlet 114, to facilitate the passage of fluid out from between the units 101.

The units 101 of the second embodiment are orientated substantially parallel to each other and are aligned in a direction which extends substantially parallel to a direction which extends substantially along an axis between the inlet 111 and outlet 114 of the respective manifolds 110, 113. In this respect, the units 101 are orientated within the apparatus 100, such that the arrangement of units 101 forms a substantially rhomboidal structure. This orientation of the units 101 serves to minimise the redirection of fluid in passing from the inlet 111 to the outlet 113 and thus further serves to minimise the pressure drop of the fluid in passing through the apparatus 100.

The membranes 102, 103 of the apparatus 100a, 100b of the first and second embodiment serve to separate a fluid flow, such as blood from a gas flow, such as air or a mixture of oxygen and carbon dioxide. In the embodiment illustrated, the blood is passed between the first membrane 102 of one unit and the second membrane of an adjacent unit, and the gas is passed between the first and second membranes of the respective unit 101. Accordingly, the support members 105 on the membranes 102, 103 remain separated from the blood flow and thus do not influence the blood flow through the apparatus 100a, 100b.

In an alternative embodiment which is not illustrated, the support member comprises a substantially planar sheet of loosely woven material (not shown), such as the Melfab non-woven fabric of composition 70% polypropylene and 30% polyethylene, having a high porosity compared with the first and second membranes. The first and second membranes 102, 103 are bonded along a periphery thereof to the loosely woven material (not shown) to define an alternative gas/fluid exchange unit (not shown). In this respect, the exchange apparatus according to the alternative embodiment is substantially the same as the first embodiment, however, the exchange apparatus according to the alternative embodiment comprises a plurality of the alternative exchange units (not shown) bonded together in a stacked configuration and held in spaced relation using the resin strips 106 and spacer members (not shown) of the first embodiment.

In use, oxygen-containing gas for example, is passed into the interior space of each unit 101 via the gas inlet manifold (not shown), and deoxygenated blood is passed between adjacent units 101 via the fluid inlet manifold (not shown). During this process, the oxygen is arranged to pass across the membranes 102, 103 to oxygenate the blood and the carbon dioxide within the blood will pass across the membranes 102, 103 in the opposite direction into the gas flow. The planar shape of the membranes 102, 103 provides for a close packing and thus an increased surface area for gas/fluid mass exchange, while their uncoupled nature in the fluid flow region helps minimise the development of nucleation sites for clots to form. Moreover, the blood inlet manifold (not shown) is arranged to direct the blood across the apparatus toward the blood outlet manifold (not shown) to minimise the residence time of blood within the fluid flow region and thus further minimise the development of clots.

Figure 3A:
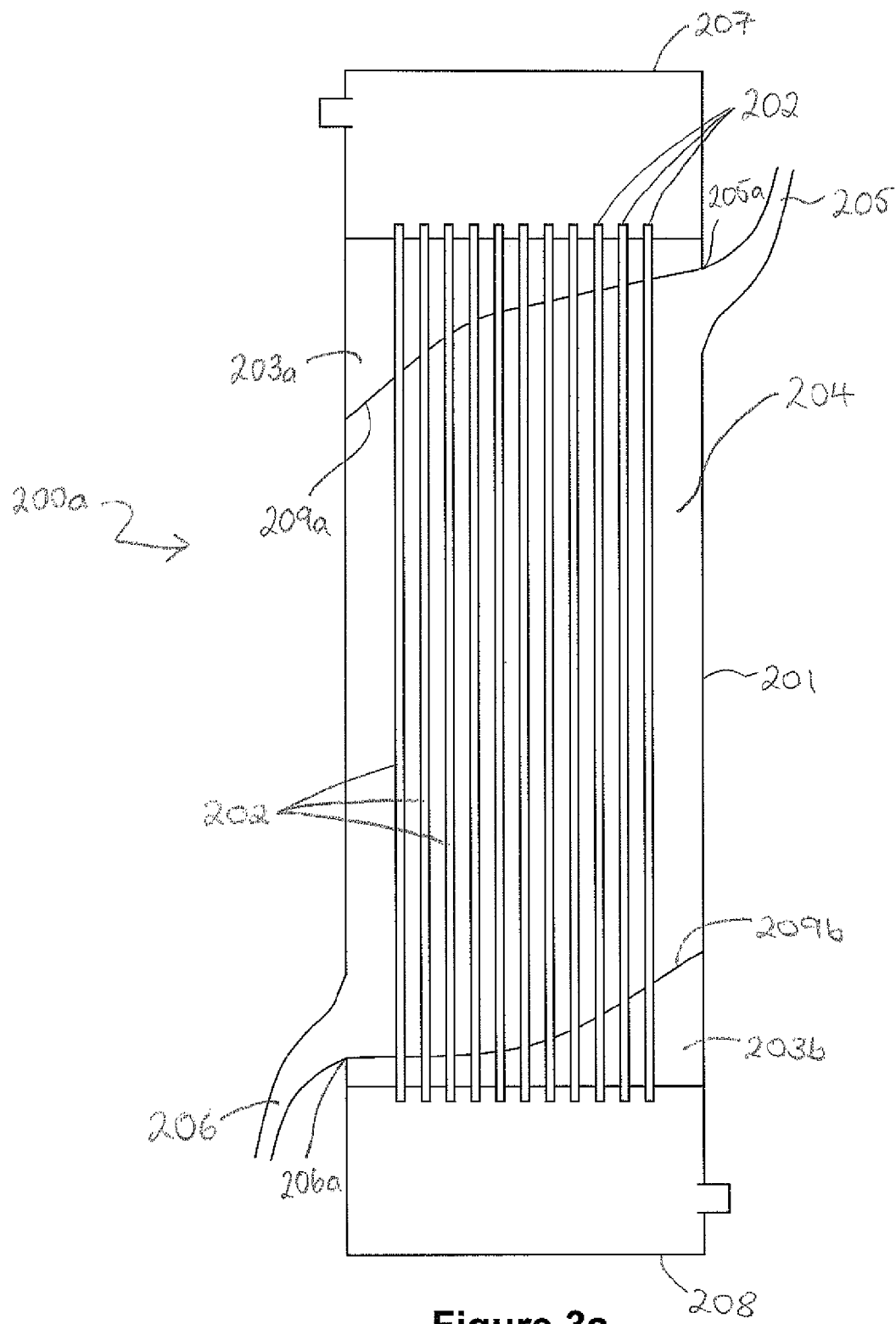
FIG. 3a is a longitudinal sectional view of a gas/fluid mass exchange apparatus according to an embodiment of the present invention; and, FIG. 3b is a longitudinal sectional view of a gas/fluid mass exchange apparatus according to an alternative embodiment of the present invention.

Referring to FIG. 3a of the drawings, there is illustrated a gas/fluid mass exchange apparatus 200a according to a third embodiment of the present invention for enabling the exchange of oxygen and carbon dioxide with a blood flow, for example. In this respect, the apparatus 200a may be used as an oxygenator to oxygenate deoxygenated blood.

The apparatus 200a comprises a housing 201 having a substantially rectangular cross-section for example, and a plurality of tubular flow ducts 202 disposed within the housing 201 which are arranged to extend between a first end and a second end thereof. The flow ducts 202 are arranged to extend substantially parallel to a longitudinal axis of the housing 201 and comprise gas permeable walls.

The shape and orientation of the flow ducts is maintained using a tensioning assembly (not shown), which is arranged to hold the flow ducts in tension. Alternatively, or in addition thereto, the shape and orientation of the flow ducts may be maintained using a plurality of support members, similar to the first embodiment.

The flow ducts 202 are held in spaced relation with respect to each other by a resin block 203a, 203b or manifold disposed proximate the first and second end of the housing 201. However, it is to be appreciated that the flow ducts may be held in spaced relation using alternative materials, such as a plastic. The resin blocks 203 are arranged to seal against the exterior of the flow ducts 202 and an interior of the housing 201 and define a fluid flow region 204 therebetween comprising an intermediate section of flow ducts 202, within which the fluid flow is substantially uniform. The blocks ensure that the portions of the fluid flow within the region 204 does not become stagnant or experience a reduced flow velocity compared with other portions, since this would otherwise encourage the development of clots.

The fluid flow region 204 is accessed via an inlet 205 disposed in a side wall of the housing 201 and an outlet 206 disposed in an opposing side wall of the housing 201, through which the fluid can pass to exit the flow region 204. The disposition of the inlet 205 and outlet 206 in opposing walls of the housing 201 further ensures that the fluid flow within the region 204 remains substantially uniform.

The first end of the housing 201 is arranged to couple with a gas inlet chamber 207 and the second end of the housing is arranged to couple with a gas outlet chamber 208. The gas inlet and outlet chambers 207, 208 are arranged in communication with the interior of the flow ducts 202 such that gas can pass from a first end of the housing 201 along the flow ducts 202, to a second end of the housing 201.

In the embodiment illustrated in FIG. 3a of the drawings, the fluid inlet 205 is angularly orientated with respect to a longitudinal axis of the housing 201 and is arranged to direct the fluid flow into the flow region 204 in a direction which is substantially along the housing 201 toward the fluid outlet 206 thereof. The fluid outlet 206 is similarly orientated at an angle to the longitudinal axis of the housing 201, such that the fluid can pass easily from the fluid flow region 204.

The apparatus illustrated in FIG. 3a may be formed by initially securing a bundle of flow ducts 202 together in a suitable spaced orientation using a soluble thread (not shown). The bundle is then positioned within the housing 201 and is fixed in position with respect to the housing 201, at the first end thereof, by immersing the first end of the housing 201 and a first end of the flow ducts 202 in a settable resin. This immersion is typically performed by tilting the housing 201 and flow ducts 202 within the resin away from the fluid inlet 205, such that once the resin has been allowed to set, the surface 209a of the resin block 203a within the housing will form an angle to the longitudinal axis thereof. The opposite end of the housing 201 is similarly immersed in a resin but tilted away from the fluid outlet 206, such that the resin surface 209b of the resin block 203b at the second end of the housing 201 and the resin surface 209a at the first end of the housing 201 cooperate to direct the fluid flow between the fluid inlet 205 and the fluid outlet 206.

In an alternative embodiment, the bundle of flow ducts 202 may be secured together in spaced relation using cross-threads disposed at opposite ends of the flow ducts 202. These cross threads are positioned upon the respective flow ducts to extend within the resin blocks 203a, 203b. In this manner, there is no requirement to remove the threads since the cross-threads become completely contained within the resin blocks 203a, 203b.

The resin surfaces 209a, 209b are arranged such they essentially match the contour of the corresponding fluid inlet and outlet 205, 206 at the interface 205a, 206a therebetween and thus facilitate the flow of fluid, such as blood, between the fluid inlet 205 and the outlet 206. The first and second end of the blocks 203a, 203b are subsequently ground to expose the opening to the flow ducts 202 at the first and second end thereof. Where a dissolvable thread has been used, a thread dissolving solution, is subsequently passed through the fluid flow region 204 to dissolve the thread (not shown) holding the flow ducts 202 together.

The matched contours at the interface between the fluid inlet and outlet with the of the fluid flow region 204, provide for a smoothly varying surface through the exchange apparatus 200 for the fluid, to thereby minimise cross-flow within the fluid flow region. The smooth flow surfaces are found to provide for an improved adhesion of coating materials such as anti-coagulants and non-coagulants, thereto and further facilitate an examination thereof to determine the coverage of the coating.

Figure 3B:
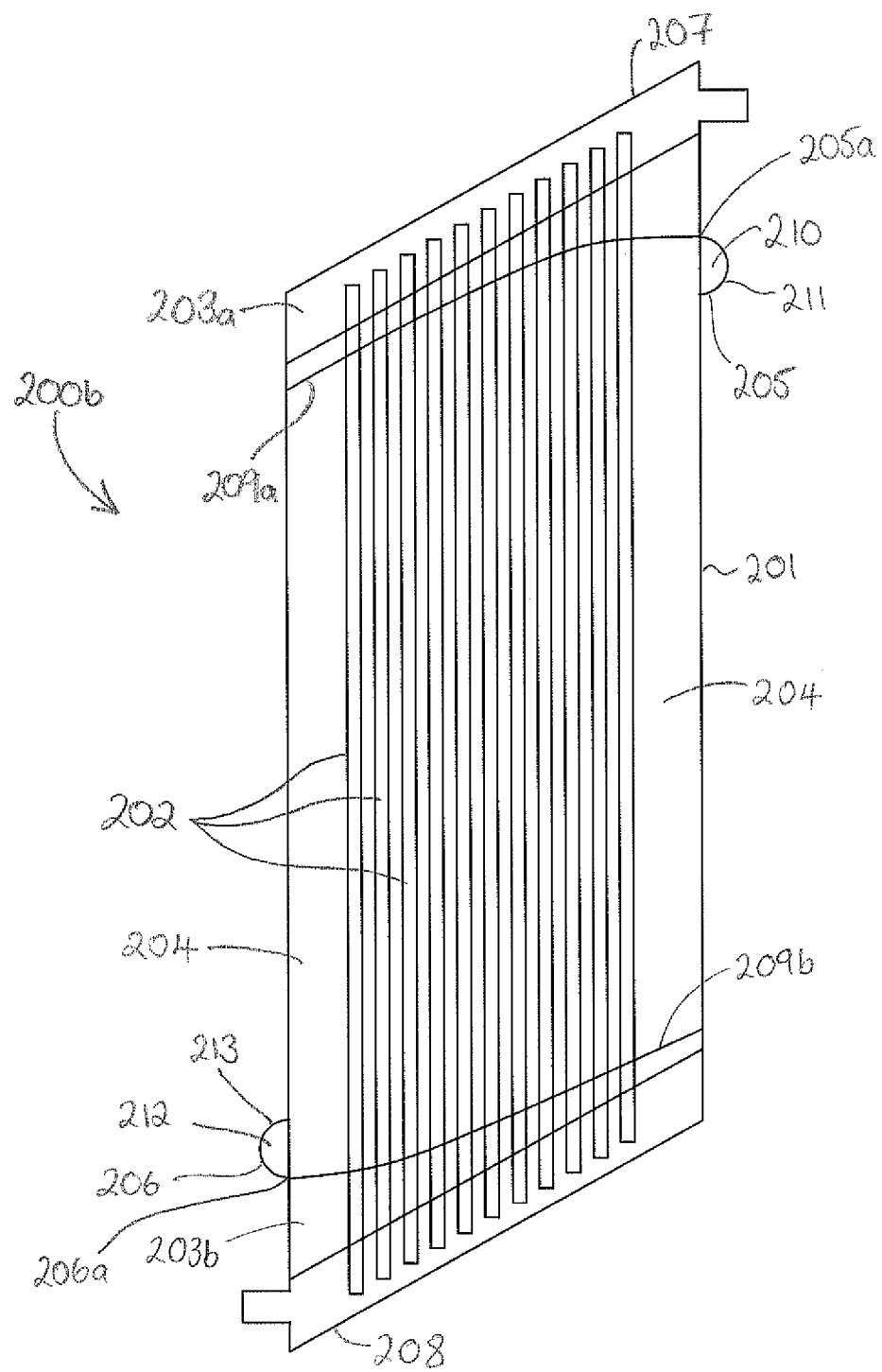

Referring to FIG. 3b of the drawings, there is illustrated a gas/fluid mass exchange apparatus 200b according to a fourth embodiment of the present invention. The apparatus 200b of the fourth embodiment is substantially the same as the apparatus 200a of the third embodiment and so like features have been referenced using the same numerals.

The fluid inlet 205 of the apparatus of the fourth embodiment is turned through substantially 90° compared with the fluid inlet 205 of the third embodiment and is arranged to direct fluid into the apparatus in a direction which extends into the page illustrated in FIG. 3b, namely across the housing 201, compared with inlet 205 of the third embodiment in which the fluid is directed substantially along the housing 201. The inlet 205 comprises an aperture 210 formed within the housing 201 and flow channel 211 formed within the housing 201, which extends across the housing 201. The channel 211 comprises a substantially semi-circular profile which reduces in width along the length thereof, from the aperture 210 to a distal end thereof. The reducing channel width is arranged to maintain the flow velocity of the fluid across the length of the channel 211 to minimise any stagnant volumes of fluid developing within the apparatus 200b.

The fluid outlet 206 of the apparatus 200b of the fourth embodiment is similarly turned through 90° compared with the fluid outlet 206 of the apparatus 200a third embodiment and is arranged to direct fluid out from the apparatus 200b in a direction which extends out of the page illustrated in FIG. 3b. The outlet 206 comprises an aperture 212 formed within the housing 201 and flow channel 213 formed within the housing 201, which extends across the housing 201. The channel 213 comprises a semi-circular profile having a width which increases along the length thereof, from a distal end toward the aperture 212, to facilitate the collection and removal of fluid from the apparatus 200b.

The fluid inlet and outlet apertures 210, 212 of the apparatus 200b of the fourth embodiment are formed in opposite sides of the housing 201 and as such, the fluid is required to change the flow direction in order to pass from the inlet 205 to the outlet 206. The contour of the flow channels 211, 213 of the inlet and outlet 205, 206 however are separately matched along one side thereof at the interface 205a, 206a with the adjacent resin surface 209a, 209b to provide for a smooth fluid flow between the inlet and outlet 205, 206.

The first and second end of the blocks 203a, 203b of the apparatus 200a, 200b of third and/or fourth embodiment may be further ground to a plane which extends substantially parallel with the adjacent resin surface 209a, 209b, such that the resulting apparatus comprises a rhomboidal structure, as illustrated in FIG. 3b of the drawings. It is found that the removal of the excess resin reduces the overall weight of the apparatus.

In use, oxygen gas for example, is passed into the gas inlet 207 of the third or fourth embodiment at the first end of the housing 201 and deoxygenated blood is passed into the fluid flow region 204 via the fluid inlet 205. Accordingly, it is evident that the flow of gas extends in a direction which is substantially parallel to the flow ducts and also, substantially parallel to a blood flow direction, similar to the first embodiment.

During this process, the oxygen is arranged to pass into the flow ducts 202 and permeate across the wall of the flow ducts 202 to oxygenate the blood. Conversely, carbon dioxide within the blood is arranged to pass across the membrane walls in the opposite direction into the flow ducts 202 and subsequently pass out of the flow ducts 202 via the gas outlet manifold 208. The spaced relation of the flow ducts 202 from each other minimises any touching of the mass transfer surfaces under the blood flow. Moreover, the blood inlet is arranged to direct the blood across the fluid flow region 204 toward the blood outlet to minimise the residence time of blood within the fluid flow region 203 and thus further minimise the development of clots.

The invention claimed is:

1. A mass exchange apparatus for introducing a gas into a fluid, the apparatus comprising:
    first and second membranes which are permeable to the gas and not permeable to the fluid;
    a frame defining left, right, top and bottom sides portions surrounding an open center;
    the first membrane arranged to extend over the open center to define a front face;
    the second membrane arranged to extend over the open center on an opposite side of the frame to define a back face, the frame thereby configured to maintain a predetermined shape and orientation of the first and second membranes;
    a strip of material disposed along the left and right side portions of the front face, whereby when two apparatuses are placed front face to back face, a gap is formed between the strips extending from the top side portion to the bottom side portion between first and second faces of adjacent apparatuses; and
    an inlet into the open center and between the first and second membranes into which the gas may be introduced;
    an outlet from the open center through which the gas may be exhausted;
    the fluid passable into the gap at the upper side portion and out of the gap at the lower side portion without a requirement of changing a flow direction of the fluid, whereby the gas may be introduced to the flowing fluid from the open center through a permeable membrane.

2. The apparatus of claim 1, further including a support material disposed upon each of the first and second membrane.

3. The apparatus of claim 2, wherein the support material is a fibrous material.

4. The apparatus of claim 1, wherein the frame is bonded to the first and second membranes.

5. The apparatus of claim 1, wherein the frame comprises a wire.

6. The apparatus of claim 1, wherein each of the first and second membranes includes a plurality of support members disposed thereon.

7. The apparatus of claim 1, wherein the predetermined shape is substantially planar.

8. The apparatus of claim 1, wherein the open center is substantially sealed from the passage of the fluid from the gap.

9. The apparatus of claim 1, wherein the first and second membranes are sealed to the frame.

10. A system comprising a plurality of apparatuses of claim 1, connected back to front.

11. The apparatus of claim 1, further including a substantially planar porous sheet having an increased porosity compared with either the first and second membrane, the sheet positionable in contact with at least one of the first and second membranes.

12. The apparatus of claim 11, the sheet including a loosely woven material.

13. The apparatus of claim 11, wherein the sheet is arranged to support the first membrane at a first side thereof and the second membrane at a second side thereof.

14. The apparatus of claim 13, wherein the first and second membranes are sealed along a respective periphery thereof to the sheet.

15. A system comprising a plurality of mass exchange apparatuses of claim 14.

16. The apparatus of claim 15, wherein the plurality of mass exchange units are spaced apart from each other.

17. The apparatus of claim 10, further comprising a gas inlet housing for passing gas into the open center of each apparatus and a gas outlet housing for passing gas out of the open center of each apparatus.

18. The apparatus of claim 1, further comprising a fluid inlet housing for passing the fluid into the gap, and a fluid outlet housing for passing the fluid out of the gap.

19. A system for introducing a first fluid into a second fluid, comprising:
 a plurality of stacked subunits, each including:
  first and second membranes which are permeable to the first fluid and not permeable to the second fluid;
  a frame defining left, right, top and bottom sides portions surrounding an open center;
  the first membrane arranged to extend over the open center to define a front face;
  the second membrane arranged to extend over the open center on an opposite side of the frame to define a back face, the frame thereby configured to maintain a predetermined shape and orientation of the first and second membranes;
  a strip of material disposed along the left and right side portions of the front face, whereby subunits are stacked front face to back face, and a gap is formed between the strips extending from the top side portion to the bottom side portion between adjacent first and second faces; and
  an inlet into the open center and between the first and second membranes into which the first fluid may be introduced;
  an outlet from the open center through which the first fluid may be exhausted;
  the second fluid passable into the gap between adjacent stacked subunits at the upper side portion and out of the gap at the lower side portion without a requirement of changing a flow direction of the second fluid, whereby the first fluid may be introduced to the flowing second fluid from the open center through the permeable membranes of adjacent stacked subunits.

20. The system of claim 19, wherein the inlets are mutually connected.

21. The system of claim 19, wherein the outlets are mutually connected.

22. The system of claim 19, wherein the gaps between adjacent subunits are interconnected at the upper side portion.

23. The system of claim 19, wherein the gaps between adjacent subunits are interconnected at the lower side portion.

24. The system of claim 19, further including a porous sheet disposed within the open center.

\* \* \* \* \*